(12) United States Patent
Gibbs

(10) Patent No.: US 6,238,879 B1
(45) Date of Patent: *May 29, 2001

(54) MICROBIOLOGICAL TESTING APPARATUS AND METHOD

(76) Inventor: David L. Gibbs, P.O. Box 4306, Santa Barbara, CA (US) 93140

( * ) Notice: Subject to any disclaimer, the term of this patent is extended or adjusted under 35 U.S.C. 154(b) by 0 days.

This patent is subject to a terminal disclaimer.

(21) Appl. No.: 09/506,921

(22) Filed: Feb. 18, 2000

Related U.S. Application Data

(63) Continuation of application No. 09/224,516, filed on Dec. 31, 1998, now Pat. No. 6,107,054.

(51) Int. Cl.[7] ............... C12Q 1/18; C12Q 1/02; C12Q 1/00
(52) U.S. Cl. ............ 435/32; 435/29; 435/4; 435/283.1; 435/287.1; 435/288.3; 422/50
(58) Field of Search ............ 435/32, 29, 4, 435/283.1, 287.1, 288.3; 422/50

(56) References Cited

U.S. PATENT DOCUMENTS

| | | | |
|---|---|---|---|
| 3,757,299 | 9/1973 | Perry | 435/32 |
| 3,811,036 | 5/1974 | Perry | 435/32 |
| 4,203,029 | 5/1980 | Kitchener et al. | 435/32 |
| 4,355,228 | 10/1982 | Sama et al. | 435/32 |
| 4,701,850 | 10/1987 | Gibbs | 435/32 |
| 4,724,215 | 2/1988 | Farber et al. | 435/32 |
| 5,290,701 | 3/1994 | Wilkins | 435/32 |
| 6,107,054 | * 8/2000 | Gibbs | 435/32 |

FOREIGN PATENT DOCUMENTS

| | | |
|---|---|---|
| 99/02645 | 1/1999 | (WO) . |
| 00/11593 | 3/2000 | (WO) . |

OTHER PUBLICATIONS

An Introduction to Automatic Image Analysis. Morton, Roger Bausch & Lomb, May, 1984, pp. 1–20.
From Image to Analysis: Object detection and measurement. Bender, Michael K. *American Laboratory*, Feb., 1984.

* cited by examiner

*Primary Examiner*—Louise N. Leary
(74) *Attorney, Agent, or Firm*—R. Neil Sudol; Henry D. Coleman

(57) ABSTRACT

An apparatus for carrying out a microbiological assay comprises a holder for holding an agar diffusion plate in operative proximity to a sensing system having one or more sensing devices, which in concert are able to read in a digital or digitizable form both pattern information created by the growth of microbial cultures on an agar gel and in particular the patterns created by the diffusion of compounds inimical to the growth of said microorganism from the loci of circular disks impregnated with the compounds, and also identification codes imprinted on the disks prior to use of the disks in a multi-disk agar diffusion assay.

19 Claims, 2 Drawing Sheets

MICROBIOLOGICAL TESTING APPARATUS AND METHOD

This is a continuation of application Ser. No. 09/224,516 filed Dec. 31, 1998 now U.S. Pat. No. 6,107,054.

BACKGROUND OF THE INVENTION

The present invention relates to a microbiological testing apparatus and an associated method. More specifically, the present invention relates to an apparatus for use in the automated antibiotic susceptibility testing of samples, such as those from patients possibly infected by a microorganism.

Agar disk diffusion is a widely recognized microbiological assay for measuring susceptibility—a parameter effectively defined by the assay itself. The susceptibility of a microorganism to a given antibiotic is essentially a description of the size of the inhibitory zone resulting from placement of a permeable disk impregnated with the given antibiotic onto an agar surface inoculated with a sample culture of the microorganism. This parameter provides a measure of the ability of the antibiotic compound to stem growth of the target culture, but it is also a complex function of diffusion constants and other kinetic factors.

Early laboratory standards for the agar diffusion assay involved qualitative evaluation by a laboratory technician, characterizing the tested bacterium's interaction with the antimicrobial agent as "susceptible", "moderately susceptible", "intermediate" or "resistant", depending on the size of the inhibition zone surrounding the antibiotic impregnated disk.

Of additional use to the clinician is a related quantitative measure of susceptibility, known as "minimum inhibitory concentration" (MIC). Although still requiring additional information to translate the parameter into a prescription for clinical practice, this quantitative measure eliminates some sources of complexity and uncertainty relative to qualitative susceptibility. A additional useful clinical parameter is the "inhibitory quotient", which expresses the ratio of the drug concentration in a particular body tissue at a lowest clinical dose to the minimum inhibitory concentration.

The MIC is ideally determined by an assay appropriately called the dilution method, which straightforwardly involves inoculating a series of test tubes with the target culture, the test tubes containing a series of dilutions of the target antibiotic. One series of test tubes therefore tests only one culture and one antibiotic, in contradistinction to an agar diffusion assay petri dish, which may test a plurality of antibiotics simultaneously with less material and expense. The advantage of the dilution method is that it provides less ambiguously interpretable quantitative results relative to the agar diffusion method, while its disadvantage is primarily its expense, both in materials and labor.

It is therefore desirable to have a device which automatically translates a dimension of an inhibition zone on an agar diffusion assay plate into a more clinically useful quantitative measure of drug-bacterium interaction, such as the MIC. Such a device is disclosed by U.S. Pat. No. 4,701,850. It is further desirable to have a device which automates the process of reading the apposite linear dimension of the inhibition zone, such devices being revealed in subsequent United States patents. The relation of the diameter of the inhibition zone to the MIC for an unknown biological agent is approximated by a linear relation, the parameters for which assumed relation for a particular antibiotic being determined by statistical estimation based on the scatter of data points whose coordinates are inhibition zone diameters and actual minimum inhibitory concentrations determined by dilution assay for a particular microorganism, the relation being assumed linear and being assumed to persist for untested organisms.

Since a number of different antibiotics are simultaneously tested against an unknown culture on a single agar plate and since these antibiotics are characterized by different values of the linear parameters relating inhibition zone dimensions to estimated MIC, and by differing values of the measured dimension of the inhibition zone in a given test, it would be advantageous to have a method of associating the zone surrounding a given antibiotic disk with the subject antibiotic compound without further operator intervention or opportunity for human error.

OBJECTS OF THE INVENTION

An object of the present invention is to provide an improved apparatus and/or associated method for microbiological testing.

A further object of the present invention is to provide a microbiological testing apparatus and/or method which enables automatic determination of a susceptibility of a microorganism to an antibiotic agent.

An additional object of the present invention is to provide such a microbiological testing apparatus and/or method which is easy to use.

It is a supplemental object of the present invention to provide such a microbiological testing apparatus and/or method which is inexpensive to use.

A particular object of the present invention is to provide an essentially automated microbiological testing apparatus and/or method wherein a dimension of an inhibition zone associated with an antibiotic impregnated disk on an agar plate is measured automatically.

A more particular object of the present invention is to provide such a microbiological testing apparatus and/or method which facilitates association of a microorganism susceptibility measurement with a particular antibiotic agent.

These and other objects of the present invention will be apparent from the descriptions and illustrations provided herein.

SUMMARY

An apparatus for carrying out a microbiological assay in accordance with the present invention comprises a holder for holding an agar diffusion plate in operative proximity to a sensing system having one or more sensing devices, which in concert are able to read in a digital or digitizable form both pattern information created by the growth of microbial cultures on an agar gel, and in particular the patterns created by the diffusion of compounds inimical to the growth of said microorganism from the loci of circular disks impregnated with the compounds, and also identification codes imprinted on the disks prior to use of the disks in a multi-disk agar diffusion assay. In a preferred embodiment, this sensing system takes the form of a single digital camera, the pattern information being stored in an intermediate form as a single digital image. Other embodiments are possible without departing from the spirit of the invention, for example, a laser scanner able to simultaneously locate and measure regions of distinct reflectance on the agar plate corresponding reduced microbial growth zones, and able to read codes on the diffusion disks, such as a bar code.

The pattern information is transmitted from the sensing system to a processing system which uses pattern recognition and processing software in order to identify and measure the diameter of a growth inhibition zone, and decode the antibiotic identification code present on the impregnated disk which lies in and gives rise to the growth inhibition zone. The processing system then provides, in a machine readable form suitable for further processing, a list whose entries include pairs of a) identifiers of the compounds present on the disks and b) the numerical diameters of the associated inhibition zones. In a preferred embodiment, the processing system is further used to estimate quantitative susceptibility parameters using as inputs the paired inhibition zone diameters and antibiotic identifiers and also a database relating inhibition zone diameters to known values of quantitative susceptibility parameters. Such a database may most simply take the form of linear regression coefficients for each compound for which there is sufficient prior data.

It is to be noted that the antibiotic identification codes provided on the diffusion disks may take any of a number of different forms including, for instance, bar codes, color codes, alphanumeric characters, or other symbols. As noted above, the sensing system of the microbiological testing apparatus or method in accordance with the present invention may include devices which are equivalent to a digital camera, for example, a video camera or a linear scanner such as a linear sensor mounted for movement relative to a two-dimensional target such as a petri dish.

A microbiological testing apparatus and/or method in accordance with the present invention enables automatic determination of a susceptibility of a microorganism to an antibiotic agent. The microbiological testing apparatus and/or method of the present invention is easy to use and relatively inexpensive. The microbiological testing apparatus and/or method facilitates association of a microorganism susceptibility measurement with a particular antibiotic agent. Costs are reduced insofar as the need for microbiological testing personnel is decreased. In addition, reliability of measurement data, particularly with respect to the association of antibiotic susceptibilities with particular antibiotics, is increased.

DETAILED DESCRIPTION

Figure 1:
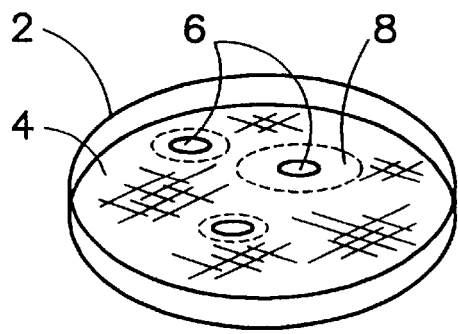
FIG. 1 is a perspective view of a petri dish containing a microbial diffusion assay in progress.

A petri dish 2, FIG. 1, contains an agar growth medium 4 on which are disposed various antibiotic diffusion disks 6. The growth medium has been inoculated with a dispersion of microorganism in a liquid, a colloid which will herein be described as a solution (not illustrated). FIG. 1 illustrates a situation subsequent to inoculation and a standardized growth period, following which the surface of the agar is partially covered by a microbial culture (cross-hatching), recognizable in a visible and machine detectable alteration in the optical properties of the agar surface. The culture is interrupted by substantially annular inhibition zones 8 surrounding each of the antibiotic diffusion disks.

Figure 2:
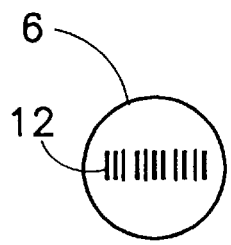
FIG. 2 is a plan view of a single antibiotic diffusion disk.

As shown in FIG. 2, an antibiotic diffusion disk 6 is marked with a code 12, which identifies the type of antibiotic contained in the disk. Code 12 may take the form of a bar code. Other coding schemes may be utilized, including but not limited to bull's eye codes, and ordinary text, which may be read by means of character recognition software.

Figure 3:
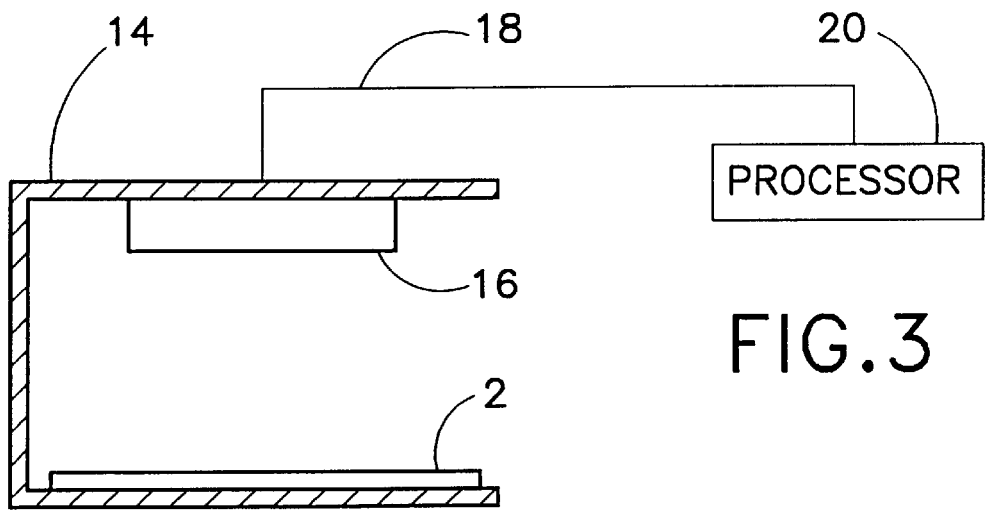
FIG. 3 is partly a schematic elevation view of a moriobiological testing apparatus in accordance with the present invention and partly a functional block diagram.

Petri dish 2 is supported by a frame 14, FIG. 3, which holds a sensing system 16 in fixed geometric relation to the petri dish. An output of said sensing system 16 is fed via a control and data line or bus 18 to a processing system 20.

Figure 4:
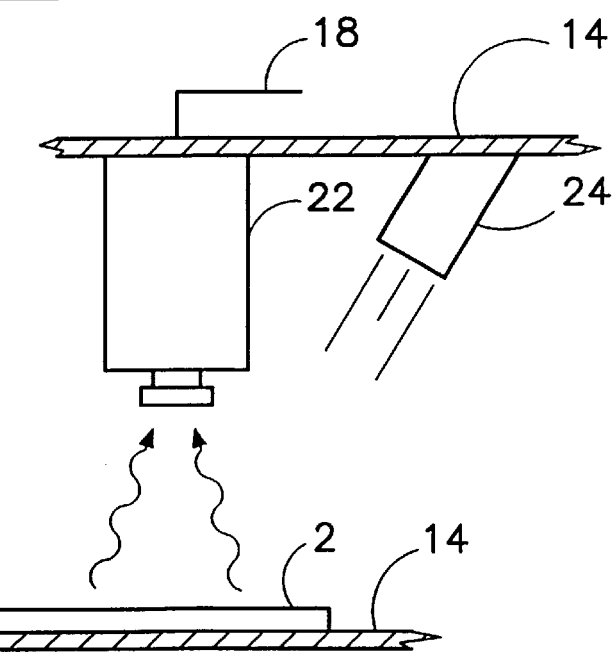
FIG. 4 is a schematic elevation view showing a particular embodiment of a sensing system included in a microbiological testing apparatus in accordance with the present invention.

In a particular embodiment sensing system 16 may be an optical monitoring device. In particular, sensing system 16 may take the form of digital camera 22, illustrated in FIG. 4. Such an embodiment also advantageously incorporates a light source 24.

Figure 5:
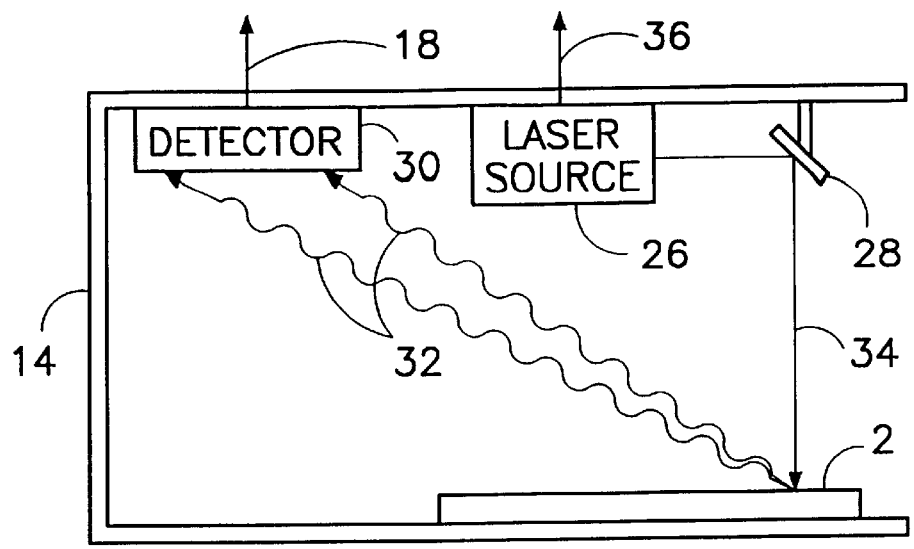
FIG. 5 is a schematic elevation view showing another embodiment of a sensing system.

In a further embodiment shown in FIG. 5, a laser beam 34 from a laser 26 may be raster scanned over the surface of the agar plate 2 via a movable reflector 28. Scattered light 32 is detected by detection means 30, which is connected to processing system 20 via control and data line 18. Movable reflector 28 is operatively connected to processing system 20 via a second control and data line 36, which may be embodied as a portion of a common control and data bus 18. Synchronization information is thereby available to processing system 18, allowing an image to be built up of regions of varying reflectance corresponding to flourishing microorganism, inhibition zones, and diffusion disks. Following a preliminary scan identifying gross features of the plate, processing system 20 can direct more detailed scanning of code regions 12 on diffusion disks 6 in order to facilitate reliable disk identification.

Figure 6:
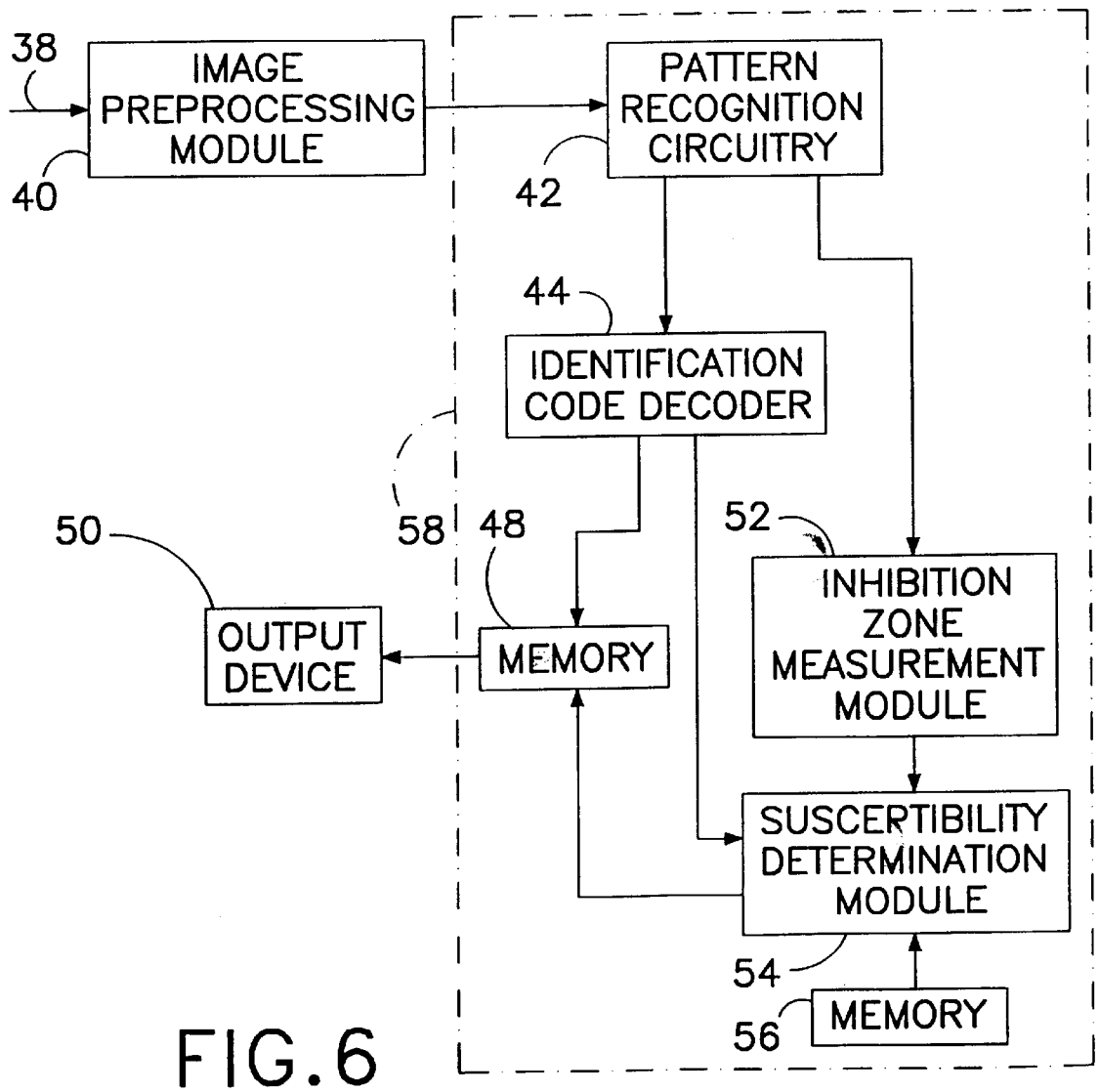
FIG. 6 is a block functional diagram illustrating data flow within the invention.

As illustrated in FIG. 6, image information from an optical sensing or scanning device such as a digital camera or a plurality of optical detectors such as two or more linear color arrays is transmitted over one or more leads 38 to an image preprocessing module 40. Module 40 processes the raw data to at least determine areas of generally similar reflectance values and to identify such contiguous areas and distinguish them from other areas on the surface of petri dish 2 that have different optical reflectance values. The preliminarily processed optical data is transmitted from module 40 to a pattern recognition circuit 42 which analyzes the data to determine which areas are disks, which areas are growth inhibition zones and which areas are colonized by microbes. Circuit 42 is connected on a downstream side to an identification code reader 44 which identifies or reads the identification codes on the disks to determine which antibiotics the disks are carrying. To that end, code reader includes a table (not separately illustrated) of possible codes and the corresponding antibiotics in human readable format. This information is stored in a buffer or memory 48 prior to being converted into human readable form via an output device 50 such as a printer, a floppy disk drive, a magnetic tape drive, or even a video monitor.

Pattern recognition circuit 42 is also connected on a downstream or output side to a inhibition zone measurement module 52. Module 52 determines a dimension of each inhibition zone recognized by circuit 42. The dimension may be a diameter or an area. Module 52 is adapted for determining where a inhibition zone ends and microbe colonization begins.

Inhibition zone measurement module 52 and pattern recognition circuit 42 are connected at outputs to a susceptibility determination module 54 which consults a memory 56 to obtain linear regression coefficients corresponding to the identified antibiotic for determining quantitative drug concentrations such as numerical susceptibility values. These values are transmitted to memory 48 prior to being converted into human readable form via output device 50. The susceptibility values from module 54 are paired with the respective antibiotic name or symbols from code reader 44.

The various circuits and modules of FIG. 6 may be dedicated circuits which are hardwired to perform the described functions. Alternatively, the various circuits and modules of FIG. 6 may be generic digital microprocessor circuits as modified by programming to perform the described functions. In most applications, a microprocessor 58 is programmed to perform image preprocessing, image component recognition, identification code reading, inhibition zone measurement, susceptibility computation, and output interfacing.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method for carrying out a microbiological assay, comprising:
   providing a plurality of diffusion disks each carrying a respective antibiotic agent and each having an identification code identifying the respective antibiotic agent;
   depositing a microbial solution on a nutrient medium;
   placing said disks in contact with said medium;
   operating at least one scanning device to automatically read the identification codes into a processing system and, after the placing of said disks and the depositing of said microbial solution, to acquire information concerning microbe-growth inhibition zones surrounding said disks and read said information into said processing system; and
   operating said processing system to decode said identification codes and thereby determine the antibiotic agents on said disks and associate the determined antibiotic agents with the respective information concerning microbe-growth inhibition zones in an output.

2. The method defined in claim 1 wherein said scanning device is a camera.

3. The method defined in claim 2 wherein said camera is a digital camera.

4. The method defined in claim 3 wherein the operating of said camera to detect said growth inhibition zones and to read said identification codes into said processing system is undertaken after growth of said microbe on said medium.

5. The method defined in claim 4 wherein the operating of said camera includes generating a digitized image of said disks and feeding said digitized image to the processing system, said identification codes being contained in said digitized image, the operation of the processing system to identify the antibiotic agents on said disks including analyzing said digitized image to determine said identification codes.

6. The method defined in claim 1 wherein said scanning device is taken from the group consisting of a solid-state imaging device providing digital output, a solid-state imaging device providing analog output, and a laser scanner.

7. The method defined in claim 1 wherein the operating of said scanning device includes generating a digitized image of said disks and feeding said digitized image to said processing system, said identification codes being contained in said digitized image, the operating of the processing system to identify the antibiotic agents on said disks including analyzing said digitized image to determine said identification codes.

8. The method defined in claim 1, wherein said output is further processed by said processing system to yield a quantitative measure of susceptibility.

9. An apparatus for carrying out a microbiological assay utilizing a plurality of drug diffusion disks each carrying a respective antibiotic agent and each having an identification code identifying the respective antibiotic agent, wherein said disks are placed in contact with a nutrient medium and a microbial solution is deposited on said medium, said apparatus comprising:
   at least one monitoring device for detecting microbe-growth inhibition zones arising about the diffusion disks after placement of the disks in contact with the nutrient medium and the deposition of the microbial solution on the medium and for detecting the identification codes on said disks; and
   a processing system operatively connected to said monitoring device, said processing system being programmed to identify the antibiotic agents on said disks in response to information from said monitoring device, said processing system being additionally programmed to determine the respective diameters of said microbe-growth inhibition zones.

10. The apparatus defined in claim 9 wherein said monitoring device is taken from the group consisting of a solid-state imaging device providing digital output, a solid-state imaging device providing analog output, and a laser scanner.

11. The apparatus defined in claim 9 wherein said processor is additionally programmed to quantify susceptibility of said microbe to each of the antibiotic agents.

12. The apparatus defined in claim 9 wherein said monitoring device is a digital camera including means for generating a digitized image of said disks and the identification codes thereon, said means for generating being operatively connected to said processing system for feeding said digitized image thereto, said processing system including generic integrated circuits modified by programming to analyze said digitized image to determine said identification codes.

13. The apparatus defined in claim 10, further comprising an output peripheral generating an output listing, in human-readable format, the antibiotic agents and a quantified measure of the susceptibility of said microbe to each of the antibiotic agents.

14. The apparatus defined in claim 9, further comprising an output peripheral generating an output listing, in human-readable format, of the antibiotic agents and the susceptibility of said microbe to each of the antibiotic agents.

15. An apparatus for carrying out a microbiological assay utilizing a plurality of drug diffusion disks each carrying a respective antibiotic agent and each having an identification code identifying the respective antibiotic agent, wherein said disks are placed in contact with a nutrient medium and a microbial solution is deposited on said medium, said apparatus comprising:
   optical monitoring means for optically detecting microbe-growth inhibition zones appearing about the diffusion disks after placement of the disks in contact with the nutrient medium and the deposition of the microbe on the nutrient medium;

code determination means for determining the identification codes on the disks after placement thereof in contact with the nutrient medium; and analyzing means operatively connected to said code determination means and said monitoring means for analyzing a dimension of each of the microbe-growth inhibition zones, identifying the associated antibiotic, and quantifying susceptibility of said microbe to each of the antibiotic agents.

16. The apparatus defined in claim 15, further comprising output means operatively connected to said code determination means and said analyzing means for providing an output in human readable format, said output listing the antibiotic agents and the susceptibility of said microbe to each of the antibiotic agents.

17. The apparatus defined in claim 15 wherein said optical monitoring means is taken from the group consisting of a solid-state imaging device providing digital output, a solid-state imaging device providing analog output, and a laser scanner.

18. A method for carrying out a microbiological assay, comprising:

providing a plurality of diffusion disks each carrying a respective antibiotic agent and each having an identification code identifying the respective antibiotic agent;

depositing a microbial solution on a nutrient medium;

placing said disks in contact with said medium;

after the placing of said disks, scanning at least said disks with a digitizing optical imaging device;

reading the resulting digitized image into a processing system; and operating said processing system at least partially as an image analyzer to automatically determine the antibiotic agents on said disks from the respective identification codes.

19. The method of claim 18 wherein said processing system is further operated to automatically determine microbe-growth inhibition zones surrounding said disks and quantify susceptibility of said microbe to each of the antibiotic agents.

* * * * *